US012751614B2

(12) United States Patent
Agarwal

(10) Patent No.: US 12,751,614 B2
(45) Date of Patent: Oct. 6, 2026

(54) SPECKLE AWARE CLINICAL DECISION SUPPORT SYSTEM FOR RETINAL DISEASES

(71) Applicant: Vedaant Agarwal, Boca Raton, FL (US)

(72) Inventor: Vedaant Agarwal, Boca Raton, FL (US)

( * ) Notice: Subject to any disclaimer, the term of this patent is extended or adjusted under 35 U.S.C. 154(b) by 0 days.

(21) Appl. No.: 19/629,574

(22) Filed: Mar. 26, 2026

(65) Prior Publication Data

US 2026/0215682 A1 Jul. 30, 2026

Related U.S. Application Data

(62) Division of application No. 19/361,879, filed on Oct. 17, 2025.

(60) Provisional application No. 63/883,404, filed on Sep. 17, 2025.

(51) Int. Cl.

| | |
|---|---|
| ***A61B 3/10*** | (2006.01) |
| ***A61B 3/00*** | (2006.01) |
| ***G06T 5/20*** | (2006.01) |
| ***G06T 7/00*** | (2017.01) |

(52) U.S. Cl.

CPC ............ *A61B 3/102* (2013.01); *A61B 3/0025* (2013.01); *G06T 5/20* (2013.01); *G06T 7/0012* (2013.01); *G06T 2207/10101* (2013.01); *G06T 2207/20081* (2013.01); *G06T 2207/20084* (2013.01); *G06T 2207/30041* (2013.01)

(58) Field of Classification Search

CPC ..... A61B 5/0066; A61B 5/0073; A61B 3/102; A61B 5/7275; A61B 5/7267; A61B 3/1241; G06T 2207/10101; G06T 7/0012; G06T 2207/10016; G06T 2207/30041; G06T 2207/20084; A61F 2/82; G16H 50/70; G16H 30/40; G16H 30/20

See application file for complete search history.

(56) References Cited

U.S. PATENT DOCUMENTS

2026/0060550 A1 * 3/2026 Derakhshani ........ A61B 5/0077

FOREIGN PATENT DOCUMENTS

CN 110555845 * 9/2024 ........... G06V 10/267

* cited by examiner

*Primary Examiner* — Brandi N Thomas

(74) *Attorney, Agent, or Firm* — The Concept Law Group, PA; Scott D. Smiley; Scott M. Garrett

(57) ABSTRACT

A clinical decision support system for retinal diseases processes OCT retinal scan images to enhance certain aspects of speckle, which has been found to include relevant information that can be used to enhance the diagnosis and classification of the severity and progression of any disease found in the retina scan image. A copy of the original OCT retinal scan image is processed using a shifted window transformer block to enhance the relevant speckle information, and combine it with the original image, which is then evaluated by a trained system to classify the retinal features, including the speckle.

18 Claims, 7 Drawing Sheets

702

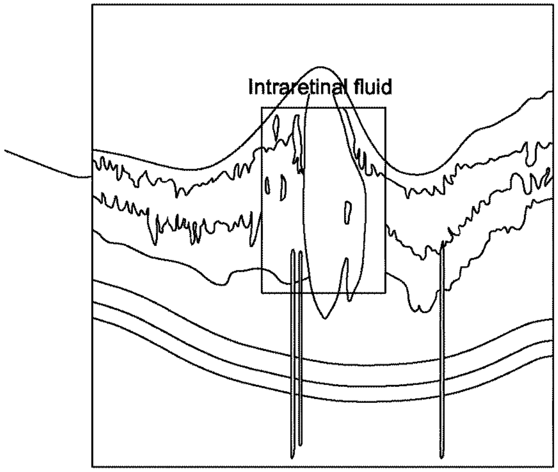

Retinal Layers Segmented

| Layer | Status | Position |
|---|---|---|
| ILM | intact | anterior |
| RNFL | intact | anterior |
| GCL | intact | anterior |
| IPL | intact | anterior |
| INL | intact | anterior |
| OPL | intact | anterior |
| ONL | intact | anterior |
| ELM | intact | posterior |
| RPE | elevated | posterior |
| Choroid | intact | posterior |

704

Clinical Summary

The OCT image reveals signs consistent with choroidal neovascularization (CNV), including pigment epithelial detachment (PED), subretinal fluid, and subretinal hyperreflective material (SHRM). These findings suggest active neovascular activity requiring further clinical evaluation and potential treatment.

706

Biomarkers and Layer Abnormalities

| Abnormality | Location | Clinical Relevance |
|---|---|---|
| PED | Sub-RPE | ○ Indicates presence of neovascularization<br>○ Elevated RPR indicating pigment epithelial detachment |
| Subretinal Fluid | Subretinal Space | ○ Associated with active CNV<br>○ Fluid RPE indicating pigment epithelial detachment |
| SHRM | Subretinal | ○ Suggests fibrovascular proliferation<br>○ Presence of subretinal hyperreflective material |

708

*FIG.7*

SPECKLE AWARE CLINICAL DECISION SUPPORT SYSTEM FOR RETINAL DISEASES

CROSS REFERENCE

This application is a divisional of U.S. patent application Ser. No. 19/361,879, filed Oct. 17, 2025, and through that application claims the benefit of U.S. Provisional Pat. App. No. 63/883,404, filed Sep. 17, 2025, the entireties of each of which are hereby incorporated by reference.

FIELD OF THE INVENTION

The present invention relates generally to optical coherence tomography systems, and, more particularly, relates to a system and method of utilizing speckle typically generated in OCT imaging to improve diagnosis.

BACKGROUND OF THE INVENTION

Retinal disease remains a leading cause of visual impairment worldwide, imposing substantial economic and personal burdens. Optical Coherence Tomography (OCT) has emerged as a cornerstone imaging modality for non-invasive visualization of retinal microstructure, enabling the early detection of pathologies such as choroidal neovascularization, diabetic macular edema, and drusen. While OCT offers high resolution, interpretation of volumetric scans often requires extensive clinician expertise, and manual analysis can be time-consuming and subject to inter-observer variability. As a result, artificial intelligence-driven clinical decision support systems have been introduced to automate image interpretation, aiming to improve diagnostic consistency and reduce workload. However, these systems face significant hurdles before routine clinical deployment, including generalizability across diverse patient populations and acquisition settings.

One example of such AI-based decision support tools focuses on single-device datasets or relies on preprocessing techniques that suppress imaging artifacts as noise. Although these approaches can enhance apparent image clarity, they frequently sacrifice subtle tissue signatures and fail to generalize across disparate OCT hardware and variable acquisition parameters. Existing classification models typically output only categorical labels, omitting information about disease stage or progression. In addition, a lack of transparent reasoning within so-called “black-box” architectures undermines clinician trust and complicates integration into established workflows. As a result, early-stage or borderline cases may remain ambiguous, and opportunities for personalized treatment planning or timely intervention can be missed.

A common problem in OCT imaging is the generation of “speckle,” which is the term given to backscattered light produced by the retinal tissue during OCT scanning. Speckle is viewed as undesirable noise, and OCT image scans are processed to try to remove speckle from the image. For example, U.S. Pat. No. 8,085,540, titled “Spectral Domain Optical Coherence Tomography System,” teaches a method reducing speckle in OCT systems by “forming a B-scan from at least a portion of . . . A-scans, wherein each resolution cell of the B-scan is generated through compounding of a subset of the A-scans, wherein at least some of the subset of A-scans are separated by at least half the diameter of a speckle cell in a direction both orthogonal and parallel to the direction of the B-scan at that resolution cell.”

Speckle characteristics depend on the specific type of OCT scan being performed, and various parameters involved. Again, since speckle is seen as undesirable noise, which is dependent on the equipment used, it is suppressed if not removed from OCT image scans in the prior art.

Studying the limitations of current frameworks reveals that few tools retain diagnostically relevant image features across diverse OCT platforms, provide objective measures of disease severity and longitudinal change, and furnish interpretable outputs to guide therapeutic decisions. A robust solution would enhance reliability in routine screening, support nuanced risk stratification, and foster clinician confidence by revealing the basis for each recommendation. Accordingly, there remains a significant need for a clinical decision support framework that is progression-aware, explainable, and capable of operating seamlessly across heterogeneous OCT systems.

A need exists to address the limitations of current solutions and provide a robust, progression-aware, and explainable tool for retinal disease management.

SUMMARY OF THE INVENTION

In accordance with embodiments of the inventive disclosure, there is provided an integrated optical coherence tomography (OCT) analytics system that includes a memory that stores computer-executable instructions, which define a speckle enhancement module and a speckle-aware transformer module. These modules are configured to enhance biologically relevant speckle information. There is also at least one processor operatively coupled to the memory that is configured, upon execution of the computer-executable instructions, to acquire an OCT scan of a retina. The OCT scan will contain a speckle pattern including biologically relevant speckle information. The processor is further configured to enhance the biologically relevant speckle information via the speckle enhancement module, to obtain a speckle-enhanced image, and provide the speckle-enhanced image to the speckle-aware transformer module to infer a disease classification chosen from choroidal neovascularization, diabetic macular edema, drusen, and an absence of disease.

In accordance with a further feature, the speckle enhancement module applies bandpass filtering, local normalization, dynamic thresholding, and anatomical-edge suppression to create a refined speckle map.

In accordance with a further feature, the speckle enhancement module further comprises a learnable gating network configured to blend the refined speckle map with an OCT B-scan according to a speckle density of the OCT B-scan.

In accordance with a further feature, there is further included computer-executable instructions defining a severity-estimation module which outputs, as a severity level, one of mild, moderate I, moderate II, or severe.

In accordance with a further feature, there is further included computer-executable instructions defining a report-generation module which incorporates into a structured clinical report a retinal-layer status table, and a biomarker relevance table.

In accordance with a further feature, the at least one processor is further configured to display the structured clinical report on a user interface together with an OCT B-scan.

In accordance with embodiments of the inventive disclosure, there is provided an unsupervised computer-implemented method of estimating retinal-disease severity from an OCT scan that includes generating, with a trained neural network, a fixed-length feature embedding of the OCT scan. The method further includes storing embeddings of a plurality of scans that are labeled as typical, and determining a centroid of the stored embeddings. The method further includes computing a Euclidean distance between the fixed-length feature embedding of the scan and the centroid. The method further includes partitioning a distribution of Euclidean distances into quartile ranges, and assigning to the scan a severity label selected from mild, moderate I, moderate II, and severe according to a quartile range in which the Euclidean distance falls.

In accordance with a further feature, the method further includes calculating a percent-deviation value for the OCT scan by dividing the Euclidean distance by an average of Euclidean distances for scans labeled with a disease and multiplying the quotient by one hundred.

In accordance with a further feature, the method further includes storing the severity label and the Euclidean distance in an electronic health record associated with a patient.

In accordance with embodiments of the inventive disclosure, there is provided a method for producing a medical scan, which includes acquiring a scan image containing speckle pattern including biologically relevant speckle information, and processing a copy of the scan image to enhance the biologically relevant speckle information to produce a speckle-enhanced image;

merging original scan image with the speckle-enhanced image to produce a transformed image. The method further comprises comparing the transformed image with other images of known diagnostic classifications to determine a diagnostic classification of the transformed image.

In accordance with a further feature, acquiring the scan image comprises acquiring an optical coherence tomography retinal scan image.

In accordance with a further feature, comparing the transformed image is performed by neural network that is trained using the other images of known diagnostic classification.

In accordance with a further feature, processing the copy of the scan image comprises applying a bandpass filter to the scan image.

In accordance with a further feature, processing the copy of the scan image further comprises applying a multi-stage shifted window transformer to the copy of the scan image subsequent to applying the bandpass filter.

Although the invention is illustrated and described herein as embodied in a speckle-aware diagnostic system and method, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

"In the description of the embodiments of the present invention, unless otherwise specified, azimuth or positional relationships indicated by terms such as "up", "down," "left," "right," "inside," "outside," "front," "back," "head," "tail" and so on, are azimuth or positional relationships based on the drawings, which are only to facilitate description of the embodiments of the present invention and simplify the description, but not to indicate or imply that the devices or components must have a specific azimuth, or be constructed or operated in the specific azimuth, which thus cannot be understood as a limitation to the embodiments of the present invention. Furthermore, terms such as "first," "second," "third," and so on are only used for descriptive purposes and cannot be construed as indicating or implying relative importance.

In the description of the embodiments of the present invention, it should be noted that, unless otherwise clearly defined and limited, terms such as "installed," "coupled," "connected" should be broadly interpreted, for example, it may be fixedly connected, or may be detachably connected, or integrally connected; it may be mechanically connected, or may be electrically connected; it may be directly connected, or may be indirectly connected via an intermediate medium. As used herein, the terms "about" or "approximately" apply to all numeric values, whether or not explicitly indicated. These terms generally refer to a range of numbers that one of skill in the art would consider equivalent to the recited values (i.e., having the same function or result). In many instances, these terms may include numbers that are rounded to the nearest significant figure. In this document, the term "longitudinal" should be understood to mean in a direction corresponding to an elongated direction of the article being referenced. The terms "program," "software application," and the like as used herein, are defined as a sequence of instructions designed for execution on a computer system. A "program," "computer program," or "software application" may include a subroutine, a function, a procedure, an object method, an object implementation, an executable application, an applet, a servlet, a source code, an object code, a shared library/dynamic load library and/or other sequences of instructions designed for execution on a computer system. Those skilled in the art can understand the specific meanings of the above-mentioned terms in the embodiments of the present invention according to the specific circumstances.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

FIG. 7 shows a clinical report that can be output by the analytics system, in accordance with some embodiments.

DETAILED DESCRIPTION

Figure 1:
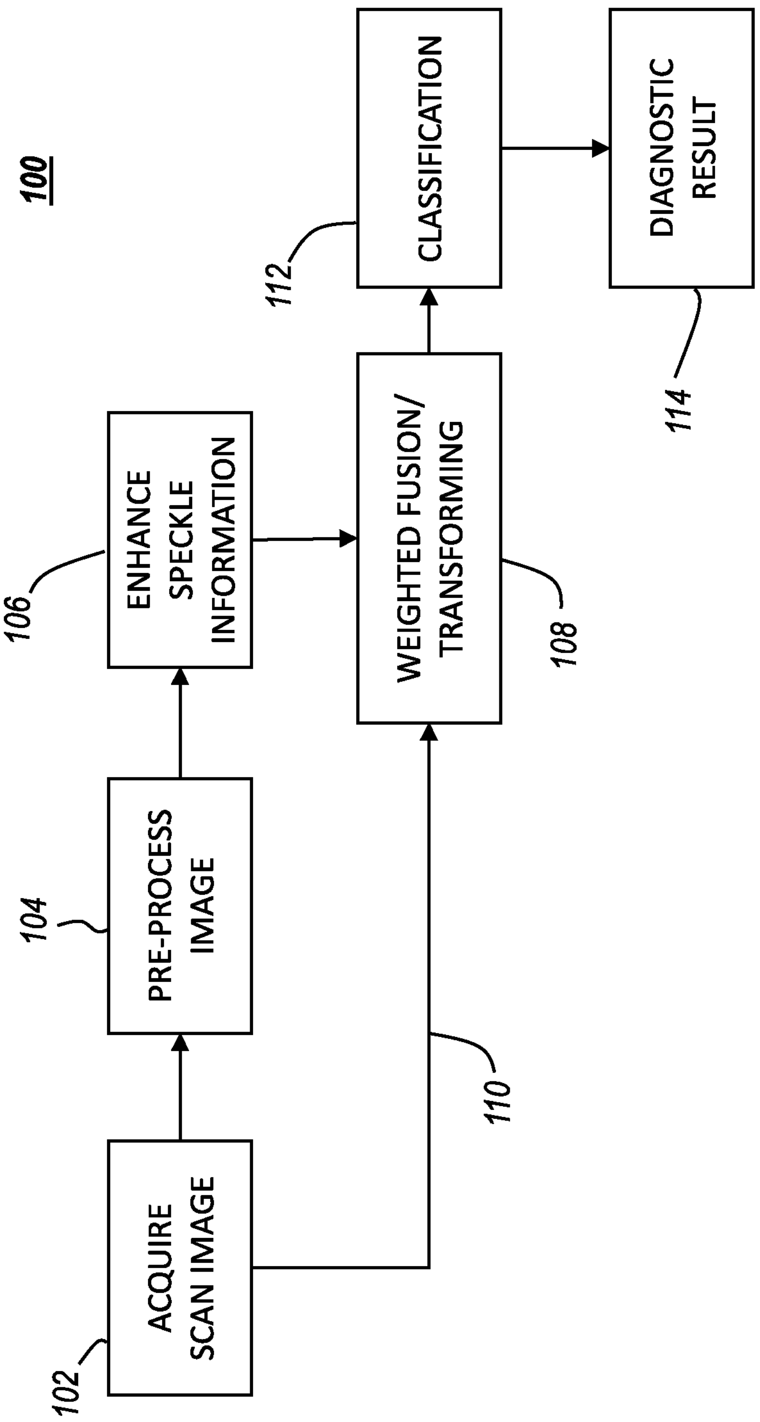
FIG. 1 shows a block process diagram for processing an OCT retinal scan image to enhance speckle information for clinical decision making, in accordance with some embodiments.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

In general, medical imaging systems that use light to generate diagnostic imaging, whether it is for OCT retinal scan imaging, or other types of electromagnetic imaging, produce a backscatter signal. In the prior art, this backscatter signal is treated as unwanted noise and efforts are made to reduce it from happening, as well as to filter it out of the image. All of these efforts have overlooked the possibility that the backscatter signal can provide further medical information that can be used to augment the clinical decision making. In the following description, backscatter is discussed in the realm of OCT retinal scan imaging, but it is important to keep in mind that the principles described herein can be applied to numerous other types of medical imaging systems in which a stimulus signal is transmitted into and through the body, or reflected back, to a sensor that captures the signal as modified by the body, and generates an image.

The exemplary speckle aware clinical decision support system of the following disclosure takes advantage of speckle; it has been found that speckle, contrary to the conventional belief that it is useless noise, has been found to contain useful diagnostic information when properly processed in accordance with the inventive disclosed herein. The general process is described in FIG. 1, which shows a block process diagram 100 for an analytics system, which, in part, executes computer-executable instructions via one or more processors. The computer-executable instruction code is stored in a memory which can include both random access memory and read only memory. The analytic system 100 can be an analytics system for processing an OCT retinal scan image to enhance speckle information for clinical decision making, in accordance with some embodiments. In general. The system processes an OCT retinal scan image, processes a copy of the image to enhance the speckle based on the specific parameters used to create the OCT retinal scan image, merges the enhanced speckle image with the original image, and then uses a deep learning engine to evaluate the merged OCT retinal scan image. The deep learning engine is a machine learning engine that has been trained using datasets of OCT retinal scan images to classify the scans into one of several diagnoses. The inclusions and use of speckle has been found by the inventor to increase the accuracy of clinical decisions over systems that suppress speckle.

Figure 2:
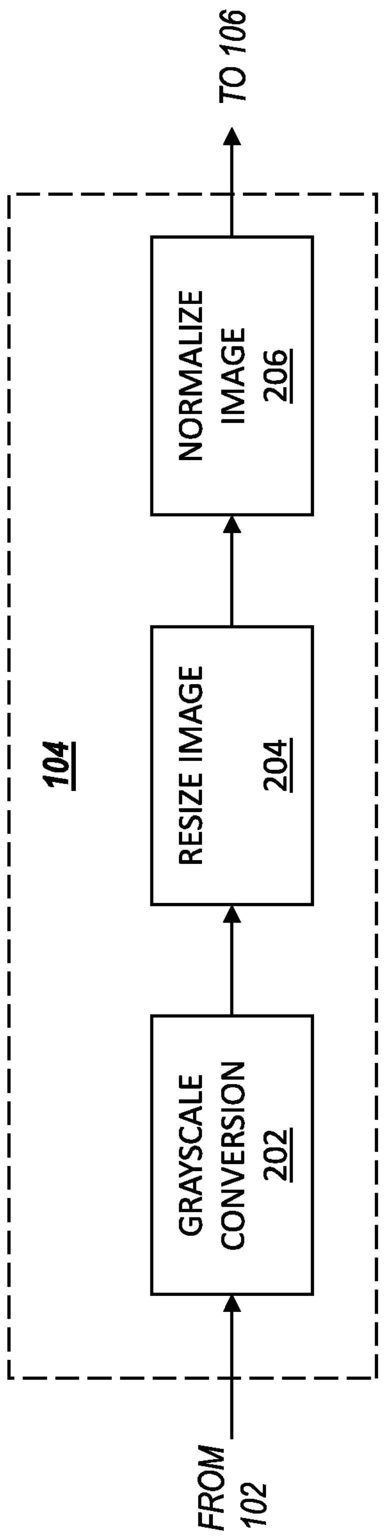
FIG. 2 shows a block pre-processing diagram for preprocessing an OCT retinal scan image, in accordance with some embodiments.

In the diagram 100, at a first block 102, the process starts by acquiring a scan image, which is produced by a medical scan. The medical scan produces a scan image by providing a stimulus signal into a body portion of a patient, and sensing the signal after it has interacted with the body portion. The sensed signal can be a reflection of the original signal, or it can be sensed on the other/opposite side of the body portion after the signal passes through the body portion. In an OCT scan system, the scan signal is an OCT retinal scan image. An OCT retinal image scan can be performed in a conventional manner using conventional OCT imaging equipment. The particulars of the OCT scanning are known and are used in the image processing to enhance the speckle content. That is, the specific parameters of the scan, such as, for example, the stimulus signal characteristics, as well as the sensor sensitivity, can be later take into account (e.g. in block 106). The output of block 102 is a digital image produced by the scanning equipment, which in the present example is an OCT scanner. The image includes indicia of anatomical structure/features, as well as biologically relevant speckle information. The raw scan image is duplicated for two different initial paths that converge at block 108, which produces a transformed image. In block 104 one copy of the raw OCT retinal scan image is preprocessed as shown in FIG. 2. For different scanning systems, different preprocessing may be used. Among preprocessing steps there is a grayscale conversion 202 to convert the raw OCT retinal scan image to grayscale. Then in image is resized in block 204, such as to a 256×256 pixel size. The resized image is then normalized in block 206 to adjust the range of pixel intensity values in the image to a specific scale to standardize the data for further processing or analysis. Normalization ensures that images with different lighting, contrast, or intensity ranges can be compared or processed consistently. Returning to FIG. 1, in block 106 the preprocessed image output from the preprocessing block 104 is processed to enhance the speckle information. One exemplary process for doing this will be described in more detail below. The output of block 106 is an image with enhanced speckle content. It has been determined by the inventor that speckle content, rather than being just noise, being generated by the backscatter of light indent on retinal tissue, actually provides some information about that retinal tissue that can be used in conjunction with ordinary OCT retinal scan image evaluation (other than eliminating speckle, of course) to produce more accurate clinical decisions. In block 108 the enhanced speckle content is merged with original OCT retinal scan image 110 to produce a merged image that is then provided to a deep learning-based classifier module in block 112. The classifier module has been trained to identify both structural features of the retina in the merged image as well as speckle information, and provide a diagnostic result 114. The diagnostic result can be, for example, normal (no indication of disease), choroidal neovascularization (CNV), diabetic macular edema (DME), or Drusen. In addition, the speckle information enables a determination of the severity and progression of disease, if any disease is diagnosed. The system can also provide a data visualization, showing where the particular merged image falls among groups of diagnoses, and a biomarker report can also be generated.

Generally, the invention provides a biologically informed OCT retinal scan image processing architecture that combines speckle-enhanced preprocessing with transformer-based visual modeling to identify both local pathology and global structural abnormalities to enable robust and anatomically sensitive classification of retinal OCT B-scans (brightness scans). Unlike conventional convolutional neural networks (CNNs) and vision transformers (ViTs) that suppress speckle as noise, the disclosed speckle aware dynamic vision transformer (SA-DVT) explicitly incorporates speckle as a diagnostic signal through a dedicated Speckle-Aware Module. This module performs a multi-stage enhancement process beginning with bandpass filtering to isolate mid-frequency components typically associated with retinal speckle, followed by local normalization to stabilize regional intensity variations and equalize contrast across spatially heterogeneous zones. Subsequently, dynamic thresholding is applied to isolate high-contrast textural elements, and anatomical edge suppression is used to attenuate sharp boundaries that are part of the retinal outline, preventing misclassification. This enhanced speckle representation is then adaptively fused with the original OCT scan via a learnable gating network/mechanism: a neural attention subnetwork that computes scan-specific blending weights based on the estimated speckle composition. The resulting input tensor integrates both anatomical and speckle-based pathology cues. This tensor is then processed by a modified Swin Transformer backbone, which utilizes hierarchical patch tokenization and shifted window self-attention to model both fine-grained retinal features and long-range spatial dependencies across the scan. FIG. 1 shows the mathematical model of the SA-DVT pipeline architecture.

The combination of biologically inspired preprocessing and global attention modeling allows the SA-DVT to recognize a wide spectrum of retinal abnormalities while maintaining interpretability through post hoc analysis such as attention rollout or gradient-based saliency. By embedding speckle awareness into the early representation stage and leveraging transformer-based reasoning, the SA-DVT achieves high generalizability across diverse imaging conditions and provides transparent, anatomically consistent predictions suitable for clinical deployment.

Figure 3:
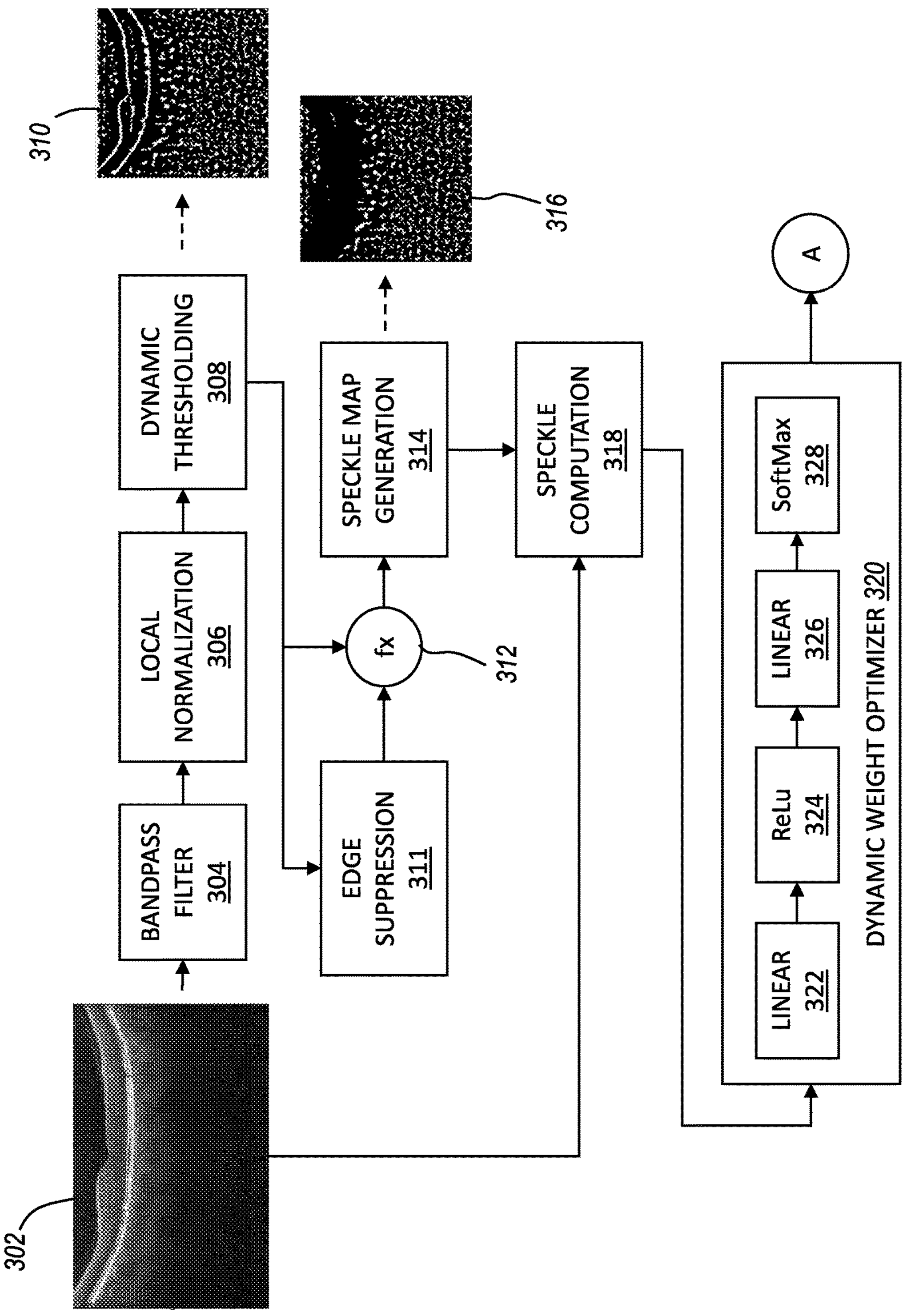
FIG. 3 shows a block process diagram for a speckle aware architecture, in accordance with some embodiments.

FIG. 3 shows a block process diagram for a speckle aware architecture, in accordance with some embodiments. An OCT retinal scan image 302 is provided first a bandpass filter 304, which combines a low pass filter and a high pass filter. This isolates the spatial frequency band where speckle noise is most prominent as speckle typically manifests in mid-frequency ranges, between low frequency anatomical contours and high frequency image noise. Since direct high pass filtering can amplify noise and degrade meaningful structural edges, a difference-of-Gaussian (DoG) approach is used to achieve bandpass localization with a controlled frequency response. Specifically, the input image 302 is processed with two Gaussian filters of differing standard deviations:

$$\text{lowpass Gaussian Filter}(\text{img}, o'_{low})$$

$$\text{highpass Gaussian Filter}(\text{img}, o'_{high})$$

where: $o'_{low}=1.0$ to preserve structural details by allowing lower frequencies to pass, and $o'_{high}=5.0$ smooths out finer detail and high frequency noise. The bandpass image is produced as the difference of the lowpass and the highpass filters. The bandpass operation 304 eliminates both low-frequency smooth regions and high-frequency noise, retaining only the mid-frequency components where speckle energy is concentrated. The resulting bandpass filtered image exhibits enhanced contrast between homogeneous retinal layers and textured speckle regions, improving visibility of diagnostically relevant speckle patterns while preserving anatomical integrity, and this facilitates downstream feature extraction in speckle-aware neural networks.

The bandpass filtered image is the normalized 306 using regional contrast normalization to account for spatial variability in intensity and texture. Due to factors such as uneven retinal thickness, heterogeneous reflectivity, and acquisition-related noise, OCT B-scans often exhibit nonuniform contrast that hinders consistent detection of speckle patterns. To correct for this, a pixel-wise normalization within fixed spatial neighborhoods is applied, thereby standardizing contrast locally:

$$\text{local mean}=\text{UnformFilter}(\text{bandpass}, \text{win size})$$

Where "bandpass" is the bandpass filtered image. The local mean mu is computed using a uniform filter of window size 15×15. Next, the local standard deviation a is estimated using the equation below, where variance is computed within the same neighborhood window and square-rooted to obtain standard deviation:

$$\text{local std}=\sqrt{\text{UniformFilter}((\text{bandpass}-\text{local}_{mean})^2, \text{win\_size})}$$

Then the normalized bandpass response is calculated using the equation below. To ensure numerical stability in flat or low-contrast regions, a minimum safe threshold $\varepsilon=10^{-6}$ is used, and a clipped denominator is computed:

$$\text{bandpass\_norm} = \frac{bandpass - \text{local\_mean}}{\text{safe\_std}}$$

The above operation ensures that the local intensity distribution is zero-centered and variance-normalized across the image. By suppressing large-scale intensity trends and emphasizing localized contrast, the operation improves sensitivity to speckle-like textural fluctuations and pathological outliers. The normalization facilitates robust and consistent speckle representation across spatially heterogeneous OCT images combined with the frequency-selective filtering from bandpass filtering.

After the normalization 306, a dynamic thresholding 308 is applied to the normalized bandpass filtered image to extract a binary speckle mask that isolates regions exhibiting statistically significant mid-frequency texture. Due to inter-scan variability in speckle strength, anatomical structure, and acquisition noise, a static threshold would be inadequate. Instead, a data-adaptive thresholding strategy based on the empirical distribution of the normalized image is used. A dynamic threshold (dynamic_thresh) using the ppp-th percentile of its pixel intensities is used:

$$\text{dynamic\_thresh}=\text{Percentile}(\text{bandpass\_norm},p)$$

where bandpass_norm is the normalized bandpass filtered image output by the normalization 306. A value of p=85 captures the upper tail of the contrast-normalized response distribution, targeting the most prominent speckle regions while excluding background texture. The percentile-based approach ensures sensitivity to scan-specific contrast dynamics without manual tuning. To further suppress weak or noisy activations, a hard lower bound is imposed by introducing a minimum absolute intensity threshold 0=0.2. The final binary speckle mask is computed using logical conjunction:

$$\text{speckle mask}=(\text{bandpass\_norm}>\text{dynamic\_thresh})^{(bandpass\_norm>min\_abs\_thresh)}$$

This formulation ensures that only pixels satisfying both relative (percentile) and absolute (minimum intensity) criteria are retained. The resulting mask 310 robustly highlights localized, high-contrast textural anomalies consistent with speckle activity, and the background clutter and low-confidence regions have been filtered out, which enables downstream modules to focus exclusively on regions with diagnostically meaningful texture.

The mask 310 is then applied to an edge suppression operation 311, which performs an anatomical-edge suppression, which helps to differentiate pathological noise from legitimate anatomical features. Sharp retinal layer interfaces, vessel contours, and lesion margins may exhibit strong gradients that mimic speckle in normalized frequency maps. Retaining such anatomical transitions within the speckle mask risks misclassification and confounds disease-specific patterns in downstream analysis. To mitigate this, we introduce an edge-aware exclusion step that explicitly filters out structural boundaries from the detected speckle regions.

A high-sensitivity edge map is first computed by applying canny edge detection to the original OCT image using a smoothing parameter $\sigma_{edge}$:

$$\text{edges}=\text{Canny}(\text{img},\sigma_{edge})$$

This process using the canny edge detector algorithm. Robust removal of adjacent edge pixels in ensured, and anatomical thickness or minor spatial shifts are accommodated, by this process, and the resulting edge map is dilated using a disk-shaped structuring element having a radius. As a result, a buffered edge region is produced as follows:

$$\text{thick\_edges}=\text{Dilation}(\text{edges},\text{disk\_radius})$$

This is recombined with the speckle mask 310 in function 312. Next, the structural edges are subtracted from the speckle mask 310 in the speckle map generation 314:

$$\text{speckle\_map\_no\_edges}=\text{speckle\_mask}(1-\text{thick\_edges})$$

This procedure eliminates high-gradient anatomical interfaces from the speckle mask 310, ensuring that only non-structural, irregular texture is retained. The result is a biologically constrained speckle representation 316 that reduces the risk of false activations near legitimate retinal boundaries, enabling more accurate and clinically interpretable downstream processing. The speckle representation 316 is then fed to a speckle computation 318 to fuse anatomical detail with speckle-enhanced information in a noise-aware manner via a learnable gating mechanism that dynamically blends the original OCT image 302 with its refined speckle map (output of 318). Since the prominence of speckle artifacts can vary widely across devices, patients, and acquisition conditions, static fusion ratios are suboptimal. The present method adapts blending weights based on the detected speckle density in each scan by quantifying speckle prevalence via a scalar value $s\in[0,1]$, representing the fraction of active pixels in the final speckle mask (excluding anatomical edges). This value, termed speckle percent, is computed as:

$$\text{speckle percent}=\frac{\text{Number of nonzero pixels in speckle\_map\_no\_edges}}{\text{Total pixels}}\times 100$$

To compute the image fusion weights, this scalar is passed through a shallow fully connected neural network that acts as a dynamic weight optimizer 320. The neural network inckudes linearizers 322, 326 and a hidden layer with rectified linear unit 324 (ReLU) activation and 8 neurons. The network output is passed through a softmax layer 328 to produce a 2-dimensional weight vector $w=[w_{oct},w_{speckle}]$ such that $w_{oct}+w_{speckle}=1$, as formulated in:

$$w=\text{Softmax}(W_2\cdot\text{ReLU}(W_1 s+b_1)+b_2)$$

Alternatively, this process can be abstracted using a compact gating module, which maps normalized speckle percentage to weights:

$$\text{weights}=LearnableGating\left(\frac{\text{speckle\_percent}}{100}\right)$$

The final blended input is then computed as a convex combination of the original image and the refined speckle map speckle_map_no_edges, as given in:

$$\text{blended}=w_{oct}\cdot\text{img}_{np}+w_{speckle}\cdot\text{speckle\_map\_no\_edges}$$

This adaptive blending framework provides several advantages. It allows the network to rely primarily on anatomical content when speckle is minimal, while emphasizing speckle-driven enhancement when textural noise is pronounced. The lightweight gating module is used only during inference and introduces negligible overhead, making it well-suited for real-time OCT processing in clinical workflows. The output of the process shown in FIG. 3 is then fed to a Swin Transformer in FIG. 4.

Figure 4:
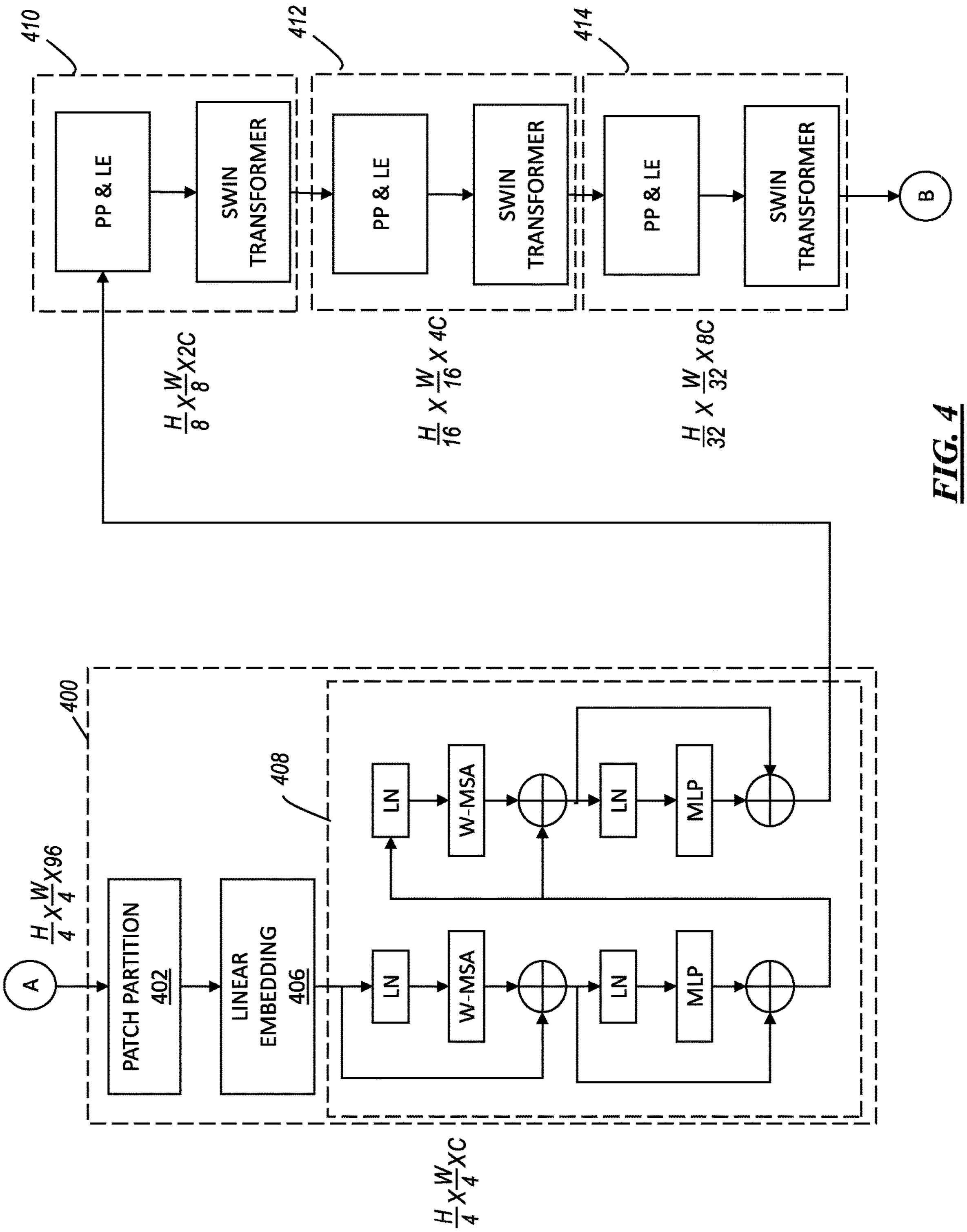
FIG. 4 shows a SWIN transformer block architecture for processing OCT images with enhanced speckle information, in accordance with some embodiments.
Figure 5:
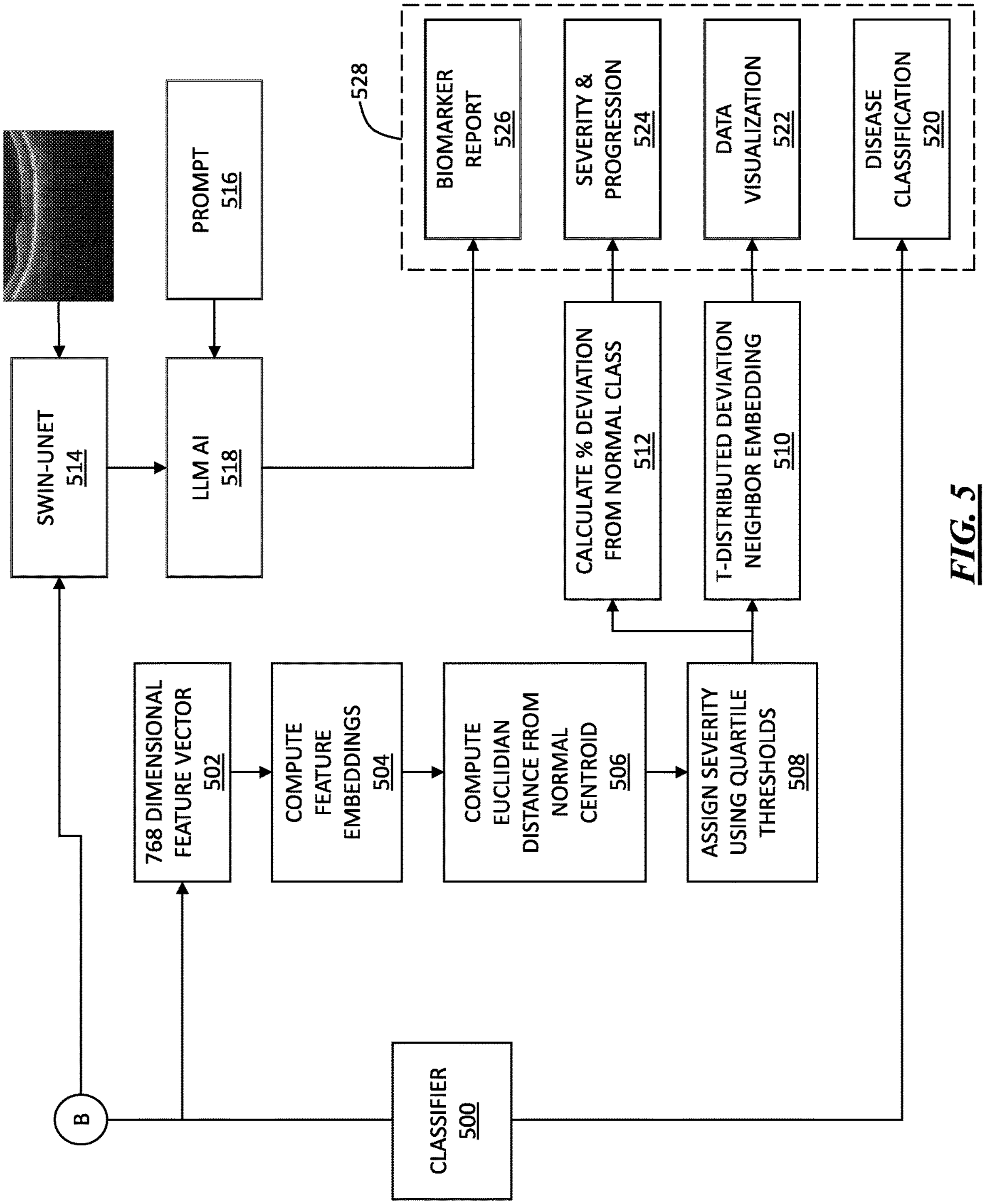
FIG. 5 shows a clinical decision support system that provides outputs regarding an OCT retinal scan image based on enhanced speckle information, in accordance with some embodiments.

FIG. 4 shows a SWIN transformer block architecture for processing OCT images with enhanced speckle information, in accordance with some embodiments. The enhanced and blended OCT image is fed into the SA-DVT backbone for feature extraction and classification. As shown in FIG. 4, the Swin Transformer processes the input image through four stages 400, 410, 412, 414. Each stage includes patch partitioning (PP) 402, linear embedding (LE) 406, and a series of Swin Transformer blocks 408 composed of alternating window-based multi-head self attention (W-MSA) and shifted window-based multi-head self attention (SW-MSA) layers, interleaved with Layer Normalization (LN) and Multi-Layer Perceptrons (MLPs). As the image progresses through these stages, the spatial resolution decreases from H/4×W/4 to H/32×W/32, while the feature dimensionality increases, capturing higher-order abstractions akin to CNNs. To ensure compatibility with grayscale blended OCT scans, the Swin Transformer's patch embedding layer is modified to accept single-channel input. As shown in FIG. 5, the final representation ("B") is passed through a dropout layer for regularization and then into a trained fully connected classifier 500 that outputs one of four diagnostic categories 520 as a diagnostic classification, which are CNV, DME, Drusen, or Normal. The classifier 500 can be, for example, a trained neural network that is trained with images of known diagnostic classifications. By combining the Swin Transformer's context-aware attention mechanisms with speckle-informed preprocessing, the SA-DVT architecture captures disease-relevant patterns that may be overlooked by architectures limited to only local or global-based reasoning.

Further in FIG. 5, an unsupervised severity estimation algorithm includes processes 502-508. This includes aggregating all embeddings from test images predicted as NORMAL and computing their arithmetic mean to define the NORMAL class center, denoted as $\mu_{NORMAL}$. Formally, if there are N embeddings from NORMAL-class images, the center is computed as:

$$\mu_{NORMAL} = \frac{1}{N}\sum_{i=1}^{N} f_i$$

Where, fi∈R768 and is the feature vector of the ith NORMAL image. This equation defines a statistical reference point in embedding space that characterizes the average anatomy of healthy retinas. For every image classified, its Euclidean distance of the NORMAL centroid, determined from the stored embeddings of images of normal retinas, is calculated through processes 502-506. This distance serves as a continuous proxy for how much the anatomical structure deviates from normal:

$$d = ||||f_{image} - \mu_{NORMAL}||_2$$

Where, $f_{image}$ is the 768-dimensional embedding of the test image in question. That is, a fixed-length feature embedding. The above equation quantifies anatomical abnormality as perceived by the model in its latent space.

All distances computed from the above equation across disease-class images are collected into a distribution. From this set of values, a process 508 computes or assigns the quartile range of retinal-disease severity, selected, for example, from the first quartile (Q1), median (Q2), and third quartile (Q3), Anything beyond the third quartile Q3 is considered in the fourth quartile Q4 as severe. These statistics define unsupervised severity thresholds that partition the disease spectrum into four clinically meaningful categories:

Mild: $d<Q1$
Moderate I: $Q1 \leq d<Q2$
Moderate II: $Q2 \leq d<Q3$
Severe: $d \geq Q3$ This unsupervised binning method assumes that greater deviation from normal correlates with increased disease burden. The use of quartiles ensures that the severity classification reflects the natural distribution of disease variation within the dataset. To compute the percent deviation from the normal class center to provide a normalized, interpretable score for each image, a ratio between the image's individual distance d and the mean distance of all disease-class images from the normal center is calculated as:

$$\overline{d}_{disease} = \frac{1}{M}\sum_{J=1}^{M}||f_j - \mu_{NORMAL}||_2$$

where, j is the embedding of the j-th disease image, and M is the total number of disease images. Equation (3) calculates the average anatomical deviation from normal among all non-healthy images, which serves as a normalization baseline. The final percent deviation from normal for each image is then computed as:

$$\text{percent deviation} = \left(\frac{d}{\overline{d}_{disease}}\right) \times 100$$

This equation expresses the image's deviation as a percentage relative to the average disease deviation. A score of 100% implies the image is as deviated from normal as the typical diseased image. From this process, the severity and progression score 524 can be provided by calculating a percent-deviation value from a normal (disease-lacking) class, as in process 512, which can be a severity estimation module.

Figure 6:
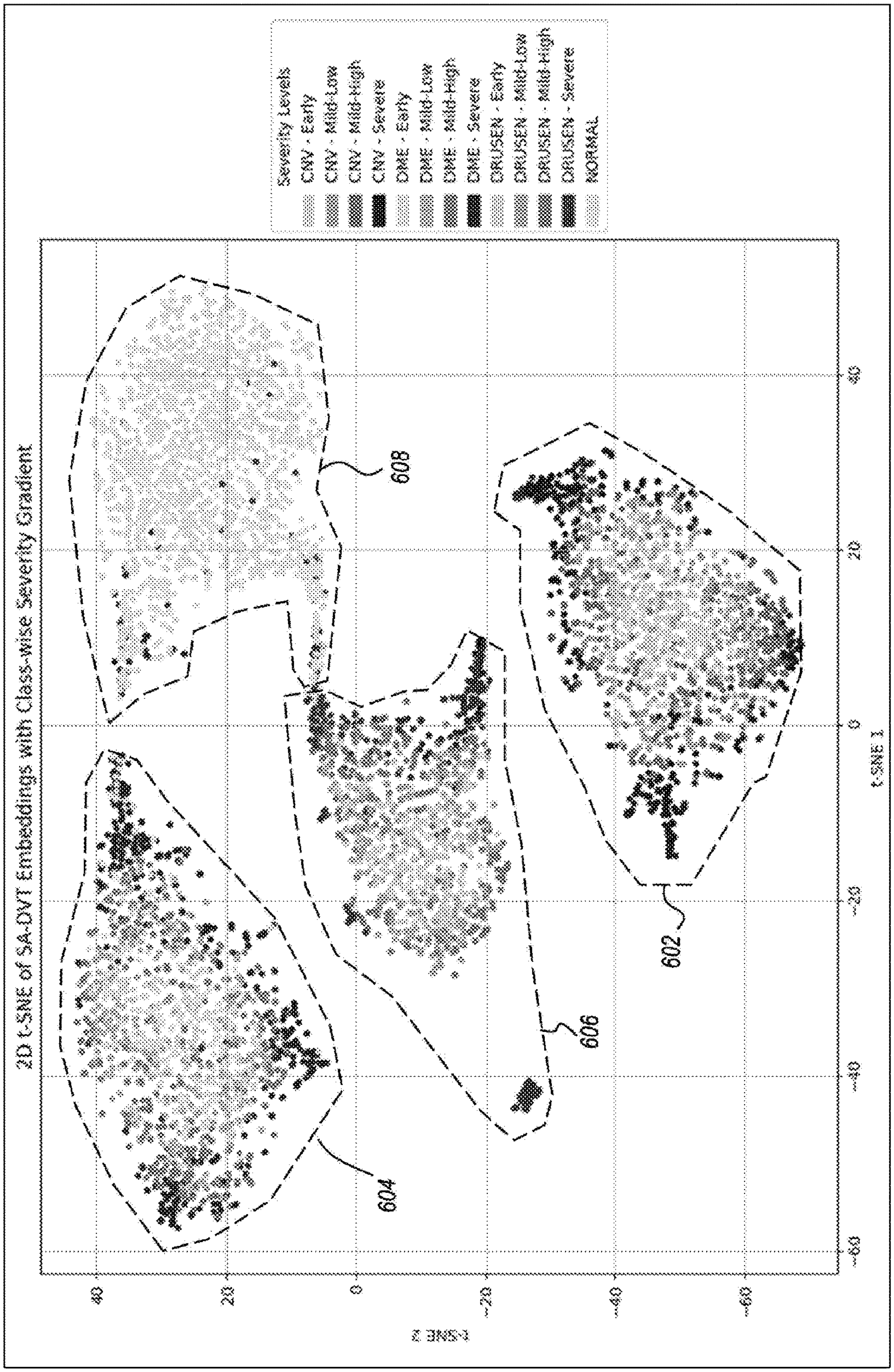
FIG. 6 shows a data visualization of a large data set of OCT retinal scan images when processed using enhanced speckle information, in accordance with some embodiments.

To interpret the structure of high-dimensional feature representations and assess intra-class variability across retinal disease categories using a visualization 522, the process employs the t-distributed Stochastic Neighbor Embedding (t-SNE) algorithm 510. t-SNE is a nonlinear dimensionality reduction technique designed to preserve the local structure of data by minimizing the divergence between pairwise similarities in high-dimensional and low-dimensional spaces. In this example, t-SNE is used to project the extracted feature vectors of OCT images into a two-dimensional space, enabling intuitive visualization of disease distributions and severity patterns, as shown in FIG. 6.

After feature extraction, each image is represented as a fixed-length vector in high-dimensional space. These vectors captured morphological and pathological characteristics relevant to disease diagnosis. To reduce dimensionality while preserving the neighborhood relationships, t-SNE is applied with the following parameters: n_components=2, perplexity=40, and a random seed=42 to ensure reproducibility. The choice of perplexity, which balances local and global aspects of the data, can be determined empirically to achieve coherent visual clustering.

The resulting two-dimensional embeddings are plotted in a scatterplot (FIG. 6) displayed in a user interface to visualize the spatial organization of disease classes and severity levels. Each point in the t-SNE plot corresponds to an individual OCT image, and points were colored according to disease class and severity subgroup. For CNV 602, DME 604, and Drusen 606, color gradients are used to represent severity stages based on quartile segmentation of Euclidean distances from each class's centroid in the feature space. Normal images 608, which indicate the absence of disease, are plotted in a distinct color to serve as a reference baseline. As can be seen, the different disease classes fall fairy closely into specific regions. This reinforces confidence in the disclosed system's internal reasoning.

In general, the outputs 528 of the disclosed system are provided as an electronic health record that allow clinicians to better interpret the information produced by the scan. The system provides interpretability based on the disease classification 520, the data visualization 522, an indication of the severity and progression 524, and the biomarker report 526, which can include a biomarker relevance table indicating the relevance of the identified biomarkers. This provides clinicians with an enhanced understanding of the patient's condition, and what can or should be done based on the image, the relative comparison of the patient's specific condition to that of others, and the disease domains in that visualization space, and the textual description prepared by the LLM AI as a biomarker report 526, which is generated by a report-generation module. FIG. 7 shows a structured clinical report that can be output by the analytics system, in accordance with some embodiments. In the report there can be included a image of the retina 702 which can include identified areas of concern (e.g. the intraretinal fluid is highlighted here). A retinal layer status table 704, a clinical summary 706, which can be output by the LLM AI, and a biomarkers and layers table 708 which can include, for example, severity labels and indicate severity levels.

The disclosed system introduces a clinically aligned CDSS that combines accurate retinal disease classification, unsupervised severity estimation, and interpretable progression analysis from a single OCT scan. The CDSS enhances generalizability through the use of the SA-DVT. The SA-DVT allows robust and highly accurate classification across diverse imaging conditions by preserving and leveraging speckle as diagnostic information. The USEA allows percent-based deviation from healthy retinal structure, offering clinicians a meaningful, quantitative indicator of disease burden without requiring labeled severity data. Furthermore, the inclusion of t-SNE provides an interpretable embedding space that visually contextualizes disease severity and inter-class relationships, fostering clinician trust in AI-generated outputs. The system addresses key barriers to AI adoption in healthcare: generalizability, explainability, and interpretability. The proposed system can be deployed in outpatient eye care, rural tele-ophthalmology programs, and longitudinal disease surveillance in chronic retinal conditions. Future extensions of this work include integrating the CDSS with electronic health records (EHRs) for real-time decision support, adapting the pipeline to other imaging modalities such as OCT-Angiography or Fundus photography, and expanding the severity estimation framework to multi-disease comorbidities. Additionally, this architecture could be generalized to other organ systems where speckle-like patterns contain diagnostic or prognostic information, further broadening its clinical impact.

The claims appended hereto are meant to cover all modifications and changes within the scope and spirit of the present invention.

What is claimed is:

1. An unsupervised computer-implemented method of estimating retinal-disease severity from an OCT scan comprising:

generating, with a trained neural network, a fixed-length feature embedding of the OCT scan;

storing embeddings of a plurality of scans that are labeled as typical;

determining a centroid of the stored embeddings;

computing a Euclidean distance between the fixed-length feature embedding of the scan and the centroid;

partitioning a distribution of Euclidean distances into quartile ranges; and assigning to the scan a severity label selected from mild, moderate I, moderate II, and severe according to a quartile range in which the Euclidean distance falls.

2. The method of claim 1, further comprising calculating a percent-deviation value for the OCT scan by dividing the Euclidean distance by an average of Euclidean distances for scans labeled with a disease and multiplying the quotient by one hundred.

3. The method of claim 1, further comprising storing the severity label and the Euclidean distance in an electronic health record associated with a patient.

4. The method of claim 1, wherein the fixed-length feature embedding is a 768-dimensional vector.

5. The method of claim 1, wherein the plurality of scans that are labeled as typical are scans labeled as normal indicating an absence of disease.

6. The method of claim 1, wherein determining the centroid comprises computing an arithmetic mean of the stored embeddings.

7. The method of claim 1, wherein the distribution of Euclidean distances is computed using embeddings obtained from scans labeled with a disease.

8. The method of claim 1, further comprising generating a two-dimensional visualization of the feature embeddings using t-distributed Stochastic Neighbor Embedding (t-SNE), with points colored according to disease class and severity label.

9. An unsupervised computer-implemented method of estimating retinal-disease severity and progression from an OCT scan comprising:

generating, with a trained neural network, a fixed-length feature embedding of the OCT scan;

storing embeddings of a plurality of scans that are labeled as normal;

determining a centroid of the stored embeddings by computing an arithmetic mean thereof, computing a Euclidean distance between the fixed-length feature embedding of the scan and the centroid;

partitioning a distribution of Euclidean distances, computed from embeddings of scans labeled with a disease, into quartile ranges;

assigning to the scan a severity label selected from mild, moderate I, moderate II, and severe according to a quartile range in which the Euclidean distance falls; and calculating a percent-deviation value for the OCT scan by dividing the Euclidean distance by an average of Euclidean distances for scans labeled with a disease and multiplying the quotient by one hundred.

10. The method of claim 9, further comprising storing the severity label, the Euclidean distance, and the percent-deviation value in an electronic health record associated with a patient.

11. The method of claim 9, further comprising generating and displaying a t-SNE visualization of the feature embeddings, with points colored according to disease class and severity level based on the quartile ranges.

12. An integrated optical coherence tomography (OCT) analytics system for estimating retinal-disease severity, comprising:

a memory that stores computer-executable instructions defining a severity-estimation module; and at least one processor operatively coupled to the memory, the at least one processor being configured, upon execution of the computer-executable instructions, to:

generate, with a trained neural network, a fixed-length feature embedding of an acquired OCT scan of a retina;

access stored embeddings of a plurality of OCT scans labeled as typical;

determine a centroid of the stored embeddings of the plurality of OCT scans labeled as typical;

compute a Euclidean distance between the fixed-length feature embedding of the acquired OCT scan and the centroid;

partition a distribution of Euclidean distances associated with OCT scans not labeled as typical into quartile ranges; and assign to the acquired OCT scan a severity label selected from mild, moderate I, moderate II, and severe according to a quartile range in which the computed Euclidean distance falls.

13. The system of claim 12, wherein the at least one processor is further configured to calculate a percent-deviation value for the acquired OCT scan by dividing the Euclidean distance by an average of Euclidean distances computed between embeddings of OCT scans labeled with a disease and the centroid, and multiplying the quotient by one hundred.

14. The system of claim 13, wherein the at least one processor is further configured to output the percent-deviation value as a quantitative indicator of deviation from typical retinal structure.

15. The system of claim 12, wherein the trained neural network comprises a Swin Transformer backbone that processes a speckle-enhanced representation of the acquired OCT scan to produce the fixed-length feature embedding.

16. The system of claim 12, wherein the at least one processor is further configured to:

apply t-distributed Stochastic Neighbor Embedding (t-SNE) to a set of fixed-length feature embeddings including the embedding of the acquired OCT scan; and generate a data visualization plot showing spatial organization of disease classes and severity levels in a reduced-dimensional space.

17. The system of claim 12, wherein the at least one processor is further configured to store the severity label and the computed Euclidean distance in an electronic health record associated with a patient from whom the OCT scan was acquired.

18. The system of claim 12, wherein the at least one processor is further configured to output, together with the severity label, a severity and progression indicator derived from the computed Euclidean distance.

* * * * *